(12) United States Patent
Sim et al.

(10) Patent No.: US 8,038,936 B2
(45) Date of Patent: Oct. 18, 2011

(54) COOKING DEVICE WITH DEODORIZATION

(75) Inventors: Sung Hun Sim, Seoul (KR); Hyun Jung Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 492 days.

(21) Appl. No.: 12/234,841

(22) Filed: Sep. 22, 2008

(65) Prior Publication Data
US 2009/0110590 A1    Apr. 30, 2009

(30) Foreign Application Priority Data
Oct. 29, 2007  (KR) .................. 10-2007-0108961

(51) Int. Cl.
| A61L 9/00 | (2006.01) |
| A61L 2/00 | (2006.01) |
| B01J 19/08 | (2006.01) |
| G01N 23/00 | (2006.01) |
| H05B 6/72 | (2006.01) |
| H05B 6/74 | (2006.01) |
| H01J 25/50 | (2006.01) |
| A23C 3/07 | (2006.01) |
| A21D 6/00 | (2006.01) |
| A23L 3/16 | (2006.01) |

(52) U.S. Cl. ........... 422/5; 422/1; 422/3; 422/4; 422/22; 422/121; 422/124; 422/186.04; 422/186.07; 422/186.1; 422/186.21; 422/305; 422/306; 219/761; 219/681; 219/730; 219/697; 219/695; 219/696; 219/746; 219/748; 219/750; 315/39.51; 99/447; 99/451; 426/240; 426/521; 426/237; 250/455.11; 250/504 R

(58) Field of Classification Search .............. 422/1, 3–5, 422/22, 121, 124, 186.04, 186.07, 186.1, 422/186.21, 305–306; 219/761, 681, 730, 219/697, 695–696, 746, 748, 750; 315/39.51; 99/447, 451; 426/240, 521, 237; 250/455.11, 250/504 R
See application file for complete search history.

(56) References Cited

U.S. PATENT DOCUMENTS

| 7,040,101 | B2 * | 5/2006 | Takeda et al. .................... 62/78 |
| 7,049,569 | B2 * | 5/2006 | Kim ............................ 219/757 |
| 2005/0178763 | A1 * | 8/2005 | Yamauchi et al. ............ 219/757 |
| 2007/0158328 | A1 | 7/2007 | Kim et al. |
| 2008/0099475 | A1 | 5/2008 | Lee et al. |
| 2008/0121635 | A1 | 5/2008 | Lee |

FOREIGN PATENT DOCUMENTS

| KR | 10-1995-0010380 B1 | 9/1995 |
| KR | 10-2000-0056754 A | 9/2000 |
| KR | 10-2003-0071677 A | 9/2003 |
| KR | 20-0315698 Y1 | 9/2003 |
| KR | 10-0712269 B1 | 4/2007 |

OTHER PUBLICATIONS

U.S. Appl. No. 12/234,964 to Lee et al, which was filed Sep. 22, 2008.

* cited by examiner

Primary Examiner — Jill Warden
Assistant Examiner — Monzer Chorbaji
(74) Attorney, Agent, or Firm — Birch, Stewart, Kolasch & Birch, LLP

(57) ABSTRACT

A cooking device includes a cooking chamber; a first deodorization region along which air from the cooking chamber flows and in which a plasma discharge is generated for removing odor-producing materials generated in the cooking chamber from the air; and a bypass region along which air from the cooking chamber flows to bypass the first deodorization region.

21 Claims, 6 Drawing Sheets

| Number | Cooking mode | Group | Ratio ($\frac{F1}{F1+F2} \times 100\%$) |
|---|---|---|---|
| 1 | Warming | Medium | 50% |
| 2 | Thawing | Weak | 0% |
| 3 | Roast | Strong | 100% |
| • | • | • | • |
| • | • | • | • |
| • | • | • | • |
| • | • | • | • |

COOKING DEVICE WITH DEODORIZATION

This application claims the benefit of Korean Patent Application No. 10-2007-0108961, filed on Oct. 29, 2007, which is hereby incorporated by reference for all purposes as if fully set forth herein.

BACKGROUND OF THE INVENTION

1. Field of the Invention

The present invention relates to a cooking device, and more particularly, to a cooking device which can which can deodorize air exhausted from a cooking chamber and control the flow of air from the cooking chamber.

2. Discussion of the Related Art

When food is cooked in a conventional cooking device and then removed from the inside of the cooking device, odor and odor-producing materials escape from the inside of the cooking device. In particular, when the cooked food is fish, a user experiences an unpleasant odor.

SUMMARY OF THE INVENTION

Accordingly, it is an object of the present invention to provide a cooking device which can remove unpleasant odor and odor-producing materials discharged from a cooking chamber and control the flow of a gas from the cooking chamber.

According to an aspect of the present invention, a cooking device includes a cooking chamber; a first deodorization region along which air from the cooking chamber flows and in which a plasma discharge is generated for removing odor-producing materials generated in the cooking chamber from the air; and a bypass region along which air from the cooking chamber flows to bypass the first deodorization region.

The cooking device may be a microwave oven. The plasma discharge may generate ozone and/or ions, and the ozone and/or ions remove the odor-producing materials from the air.

The cooking device may further include a controller that controls a first inflow amount of air containing odor-producing materials into the first deodorization region, and a second inflow amount of air containing odor-producing materials into the bypass region.

The controller may control the first inflow amount and the second inflow amount based on operating information of the cooking device. The operating information may include a plurality of cooking modes of the cooking device, and the controller may control the first inflow amount and the second inflow amount based on the plurality of cooking modes. The plurality of cooking modes may be classified into a plurality of groups based on a predicted discharge amount of odor-producing materials, and the controller may control the first and second inflow amount so that a ratio of the first inflow amount with respect to the second inflow amount increases for groups having larger predicted discharge amounts of odor-producing materials.

The cooking device may include an input unit configured to receive instructions input by a user, the controller controlling the first inflow amount and the second inflow amount according to the instructions input by the user.

The cooking device may include a second deodorization region in which air from the first deodorization region which includes residual odor-producing materials is mixed with air from the bypass region which includes odor-producing materials, for removing the remaining odor-producing materials. The plasma discharge generated in the first deodorization region may generate ozone and/or ions to remove odor-producing materials from the air, and the remaining ozone and/or the remaining ions from the first deodorization region remove the remaining odor-producing materials in the second deodorization region. The cooking device may further include an ozone removal unit that removes the remaining ozone in the air from the second deodorization region.

The cooking device may further include an ozone removal unit that removes the remaining ozone from the air downstream from the first deodorization region. A flow rate of air in the first deodorization region may be less than a flow rate of air in the bypass region. The cooking device may further include an outer casing, the first deodorization region and the bypass region being located outside of the cooking chamber and inside of the outer casing. The cooking device may further include a plasma generator located in the first deodorization region, the plasma generator including first and second discharge electrodes separated by a dielectric material located there between.

According to another aspect of the present invention, a cooking device includes a cooking chamber; a first deodorization region along which air from the cooking chamber flows and in which a plasma discharge is generated for removing odor-producing materials generated in the cooking chamber from the air; and a bypass region along which air from the cooking chamber flows to bypass the first deodorization region. No plasma discharge is generated in the bypass region, and a flow rate of air in the first deodorization region is less than a flow rate of air in the bypass region.

According to another aspect of the present invention, a method for deodorizing air in a cooking device includes exhausting air containing odor-producing materials from a cooking chamber of the cooking device; selectively directing the air from the cooking chamber to either a deodorization flow path or to a bypass flow path, or to both the deodorization flow path and the bypass flow path; and deodorizing air directed along the deodorization flow path by removing the odor-producing materials.

The deodorizing may include generating plasma discharge to produce ozone and/or ions for removing the odor-producing materials from the air. The method may further include removing ozone remaining in the air downstream from the deodorization flow path. The selectively directing the air may include automatically directing the air based on a cooking mode of the cooking device. The selectively directing the air may include directing the air based on a selection input by a user.

According to another aspect of the present invention, a method for deodorizing air in a cooking device includes exhausting air containing odor-producing materials from a cooking chamber of the cooking device; and selectively deodorizing the air from the cooking chamber by removing the odor-producing materials.

The selectively deodorizing the air may include generating plasma discharge to produce ozone and/or ions for removing the odor-producing materials from the air. The method may further include removing ozone remaining in the air after selectively deodorizing the air. The selectively deodorizing the air may include automatically deodorizing the air based on a cooking mode of the cooking device. The selectively deodorizing the air may include deodorizing the air based on a selection input by a user.

In accordance with a cooking device according to the present invention, odor and odor-producing materials generated from a cooking chamber can be removed in a first deodorization region by a plasma discharge. Further, since an exhaust gas of the cooking chamber can bypass the first deodorization region and be discharged directly to the outside, exhaust can be smooth and power consumption can be decreased.

DETAILED DESCRIPTION OF THE INVENTION

Hereinafter, the present invention will be described in detail with reference to the drawings.

The deodorization device of the present invention may be applied to any suitable type of cooking apparatus, such as a gas, electric or microwave oven. Further, the cooking apparatus of the present invention may include all kinds of devices capable of cooking food, such as a gas, electric or microwave oven.

Figure 1:
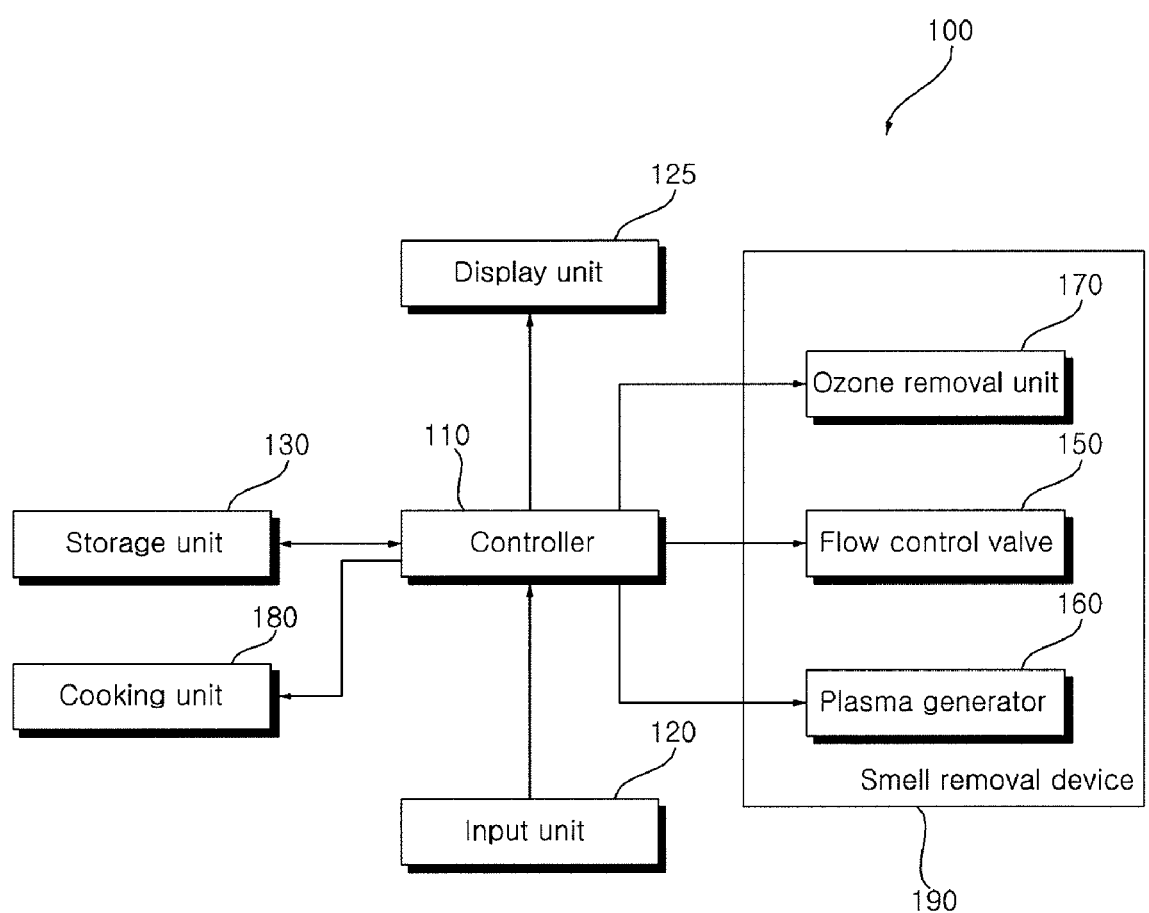
FIG. 1 is a block diagram of a cooking device according to an embodiment of the present invention.

FIG. 1 is a block diagram of a cooking device 100 according to an embodiment of the present invention. Referring to FIG. 1, the cooking device 100 includes a controller 110, an input unit 120, a display unit 125, a storage unit 130, a cooking unit 180, and an odor and odor-producing materials removal device 190. The input unit 120 receives an operating signal from a user. The cooking unit 180 cooks food based on the operating signal input by the user. The input unit 120 may have any suitable configuration, such as a button structure or a dial structure. The cooking unit 180 cooks food using any suitable devices, such as a cooling fan (not shown), a heater (not shown) or a microwave device (not shown).

The storage unit 130 stores information related to the operation of the cooking device 100. If an operating signal is received from a user, the controller 110 generates a control signal in response to the operating signal and outputs the control signal to the cooking unit 180. The cooking unit 180 cooks food according to the control signal. The display unit 125 functions to display any suitable information, such as cooking information of food or a user's input operating information, and may have any suitable structure, such as that of a LCD panel.

Figure 2:
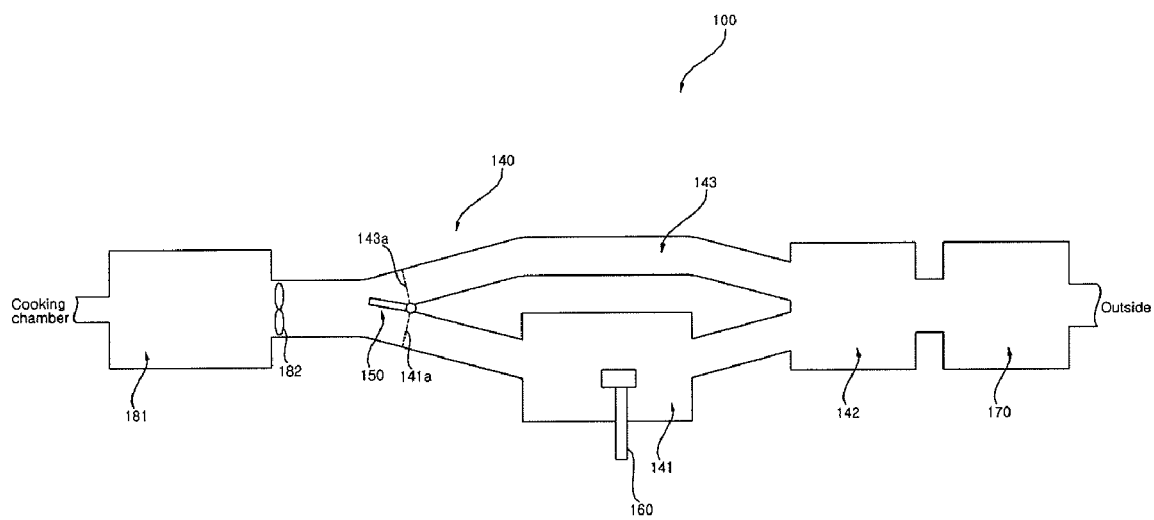
FIG. 2 is a view schematically showing an internal structure of an odor removal device shown in FIG. 1.

FIG. 2 is a view schematically showing an internal structure of the odor removal device 190 shown in FIG. 1. The odor removal device 190 functions to remove odor and odor-producing materials, discharged from the cooking chamber by a cooling fan 182, before the air is discharged to the outside.

The odor removal device 190 includes an ozone removal unit 170, a flow control valve 150, a plasma generator 160, and a casing 140.

The casing 140 defines an internal flow space, which includes a first deodorization region 141, a bypass region 143, and a second deodorization region 142. The first deodorization region 141 communicates with the cooking chamber 181. Odor and odor-producing materials discharged from the cooking chamber 181 are primarily removed in the first deodorization region 141. The bypass region 143 communicates with the cooking chamber 181, and is a region where odor and odor-producing materials generated from the cooking chamber 181 bypass the first deodorization region 141.

The flow control valve 150 is disposed at the branch of the first deodorization region 141 and the bypass region 143. The flow control valve 150 controls the inflow of a gas, which is introduced to the first deodorization region 141 (hereinafter, referred to as a "first inflow"), and the inflow of a gas, which is introduced to the bypass region 143 (hereinafter, referred to as a "second inflow"). In other words, the controller 110 controls the flow control valve 150 to adjust the first inflow and the second inflow. In the present invention, the gas may be a fluid containing odor and odor-producing materials. The odor and odor-producing materials may have a gaseous state, a solid state or liquid state. Further, the fluid may include air. In FIG. 2, it is shown that the first deodorization region 141 and the bypass region 143 are separated from each other. However, a compartment disposed within a duct structure can separate the first deodorization region 141 and the bypass region 143.

Control of the flow to the first deodorization region 141 and the bypass region 143 may be achieved with any suitable structure. For example, two flow control valves 150 may be disposed in an inflow port 141a of the first deodorization region and in an inflow port 143a of the bypass region, respectively. However, only one flow control valve 150 may be used to control the opening degree of the inflow port 141a of the first deodorization region and the inflow port 143a of the bypass region.

In the first deodorization region 141 is disposed the plasma generator 160. The plasma generator 160 generates plasma, and generates ozone and ions from air. The plasma generator 160 may have any suitable structure. An example of the plasma generator 160 is shown in FIGS. 3 and 4.

Figure 3:
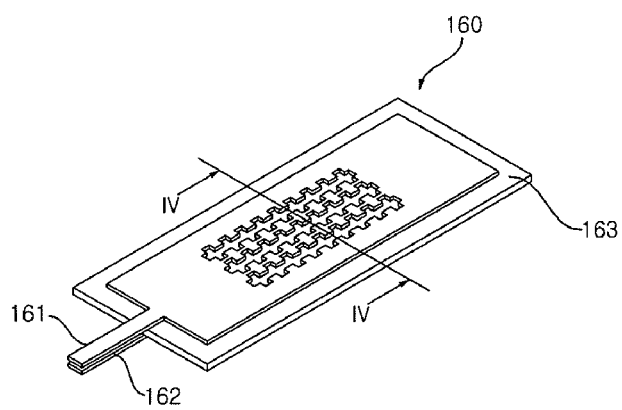
FIG. 3 is a partial perspective view of a plasma generator.
Figure 4:
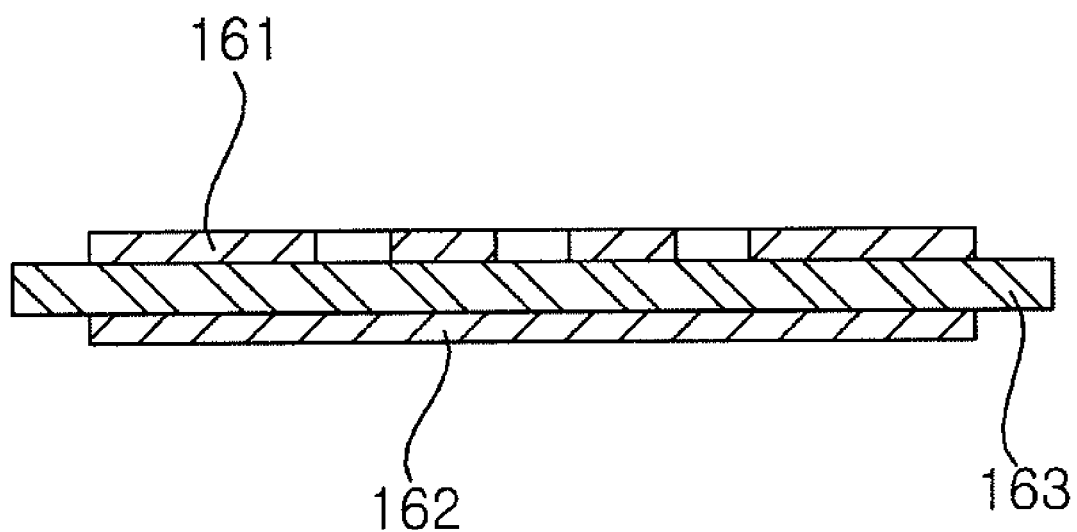
FIG. 4 is a sectional view taken along line IV-IV of FIG. 3.

FIG. 3 is a partial perspective view of the plasma generator 160. FIG. 4 is a sectional view taken along line IV-IV of FIG. 3. Referring to FIGS. 3 and 4, the plasma generator 160 includes a first discharge electrode 161, a second discharge electrode 162, a dielectric material 163, and any suitable type of voltage application unit (not shown). The first discharge electrode 161 and the second discharge electrode 162 are spaced apart from each other, and the dielectric material 163 is positioned between the first discharge electrode 161 and the second discharge electrode 162. A discharge voltage from the voltage application unit is applied to the first discharge electrode 161, and the second discharge electrode 162 is grounded. However, the construction of the plasma generator is not limited to the above construction, and may be formed in any suitable manner.

The bypass region 143 and the first deodorization region 141 are coupled to the second deodorization region 142. Odor and odor-producing materials not removed in the first deodorization region 141 and odor and odor-producing materials introduced from the bypass region 143 are removed in the second deodorization region 142 by the remaining ozone and the remaining ions, which are introduced from the first deodorization region 141. Accordingly, since odor and odor-producing materials are secondarily removed in the second deodorization region 142, the amount of odor and odor-producing materials discharged to the outside is decreased significantly. An additional plasma generator is not disposed in the second deodorization region 142. However, a plasma generator may be disposed in the second deodorization region 142 if additional odor removal is desired.

The second deodorization region 142 is coupled to the ozone removal unit 170. Though ozone is used to effectively remove odor and odor-producing materials, there is a danger that ozone may be harmful to human health when it is discharged to the outside. Accordingly, it is necessary to control the amount of ozone discharged to a set value or less. The ozone removal unit 170 breaks ozone down by heating the gas, introduced from the second deodorization region 142, to a set temperature or higher. However, the ozone removal unit is not limited to the structure described above, but the ozone removal unit 170 may remove ozone in any suitable manner.

Figures 5, 6:
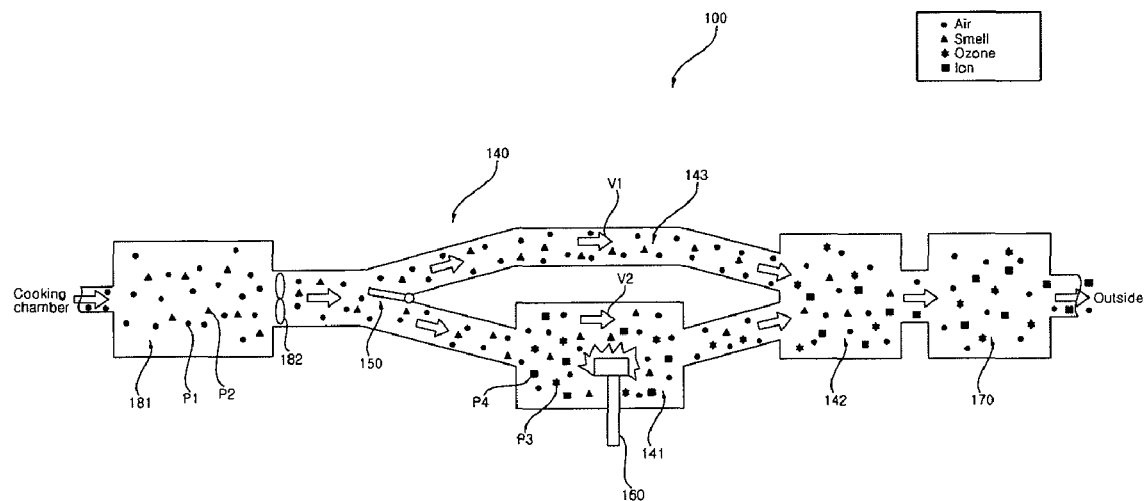
FIG. 5 is a schematic view illustrating the flow of air, odor-producing materials, ozone, and ions in a condition in which an inflow port of a first deodorization region and an inflow port of a bypass region are opened within the odor removal device of FIG. 2.
FIG. 6 is a table illustrating groups according to cooking modes and corresponding ratios of inflow amounts.

Hereinafter, a mechanism for removing odor and odor-producing materials generated in the cooking device 100 is described in detail. The flow of air P1, odor and odor-producing materials P2, ozone P3, and ions P4 within the odor removal device 190 is schematically shown in FIG. 5. Referring to FIG. 5, the flow control valve 150 opens the inflow port 141a of the first deodorization region and the inflow port 143a of the bypass region. As mentioned above, the controller 110 can control the inflow port 141a of the first deodorization region and the inflow port 143a of the bypass region to adjust the first inflow and the second inflow. The opening degree of the inflow ports 141a and 143a can be controlled automatically, depending on the mode of operation of cooking device 100, or may be controlled based on a selected preference of a user.

The controller 110 controls the opening degree of the inflow ports 141a and 143a based on operating information of the cooking device 100. The operating information may include various pieces of information, but may include cooking modes of the cooking device. A table, illustrating the cooking modes and the ratio of the first inflow F1 to a total sum of the first inflow F1 and the second inflow F2, is illustrated in FIG. 6. The table is stored in the storage unit 130.

Referring to FIG. 6, the cooking modes may include a warming mode, a thawing mode, and a roast mode. If food is cooked according to the roast mode, odor and odor-producing materials are generated in the cooking chamber 181 in great quantities. However, if food is cooked according to the thawing mode, the amount of odor and odor-producing materials generated in the cooking chamber 181 is not much. Thus, the cooking modes can be represented by a plurality of groups on the basis of a predicted discharge amount of odor and odor-producing materials. The groups include a "strong" group, a "medium" group, and a "weak" group. In the cooking modes belonging to the "strong" group (in which a large amount of odor is generated), the inflow port 143a of the bypass region is closed in order to further remove odor and odor-producing materials. However, in the cooking mode belonging to the "weak" group (in which little if any odor is generated), the inflow port 141a of the first deodorization region is closed. Flow resistance is relatively large in the first deodorization region 141 due to the presence of the plasma generator 160. Thus, the flow rate V1 of a gas in the first deodorization region 141 is smaller than a flow speed V2 of a gas in the bypass region 143. Accordingly, if a gas is discharged to the outside only through the first deodorization region 141, the amount of power necessary for the cooling fan 182 is increased. In the present embodiment, a gas including a small amount of odor and odor-producing materials does not need to pass through the first deodorization region 141, but can instead be discharged to the outside through only the bypass region 143. Consequently, the discharge amount of a gas per unit time can be increased and the amount of power necessary for the cooling fan 182 can be reduced.

In the cooking mode belonging to the "medium" group, both the inflow port 143a of the bypass region and the inflow port 141a of the first deodorization region are opened.

Instead, the first inflow and the second inflow may be operated directly by a user input or selection. A user may input an operating signal to the input unit 120 to selectively chose the amount of the exhausted air which will pass through the deodorization region 141. The controller 110 can control the first inflow and the second inflow by controlling the flow control valve 150 according to the operating signal input by the user.

Referring to FIG. 5, in the first deodorization region 141, the plasma generator 160 is operated to generate a plasma discharge. At the time of a plasma discharge, ozone P3 and/or ions P4 are generated from the air P1. The ions P4 may include various kinds of ions and may include, for example, negative ions such as hydroxide ion (OH$^-$). The ions P4 and the ozone P3 function to decompose and remove odor-producing materials through a reaction with the odor-producing materials P2 introduced to the first deodorization region 141. The amount of the odor-producing materials P2 removed may be controlled according to the amount of the ozone P3 and the ions P4 generated, and the amount of exposure or reaction time with the odor-producing materials P2. In other words, if the ions P4 and the ozone P3 are sufficiently generated by increasing the plasma discharge region and the reaction time with the odor-producing materials P2 is lengthened by increasing the internal flow region of the first deodorization region 141, the amount of the odor-producing materials P2 removed can be increased. However, a gas introduced to the bypass region 143 flows to the second deodorization region 142 without removal of any odor-producing materials from the gas.

A main source material of the smell is a mixture of C—H, wherein the ions and ozone disconnect C—H bond in the source material. The amount of removed smell is determined depending on the amount of generated ions and ozone, the reaction time of the smell, and the like.

Furthermore, the moisture is condensed and small aerosol particles are produced during the plasma discharge, and the condensed moisture and produced small aerosol particles play a role to remove the smell. Especially, the small aerosol particles directly react with the material that generates the smell thereby to produce a large quantity of CH$_3$—S radicals. The CH$_3$—S radicals disconnect the C—H bond, thus removing the smell.

In the second deodorization region 142, gas may be introduced from the first deodorization region 141 and the bypass region 143. The gas includes the remaining odor and odor-producing materials P2, the remaining ozone P3, and the remaining ions P4. In the second deodorization region 142, the remaining ozone P3 and the remaining ions P4, such as hydration ions, function to remove the remaining odor-producing materials while reacting with the remaining odor-producing materials P2. Further, as the remaining odor-producing materials P2 are removed, part of the remaining ozone P3 is also removed. Accordingly, not only the amount of the ozone P3 discharged to the outside can be reduced, but also the amount of the odor-producing materials P2 discharged to the outside can be reduced.

The gas discharged from the second deodorization region 142 is introduced to the ozone removal unit 170. In the ozone removal unit 170, the remaining ozone P3 may be removed. Accordingly, the amount of the ozone P3 discharged to the outside can be kept to a predetermined value or less. However, the ozone removal unit is not necessarily required, and may be omitted.

Figure 7:
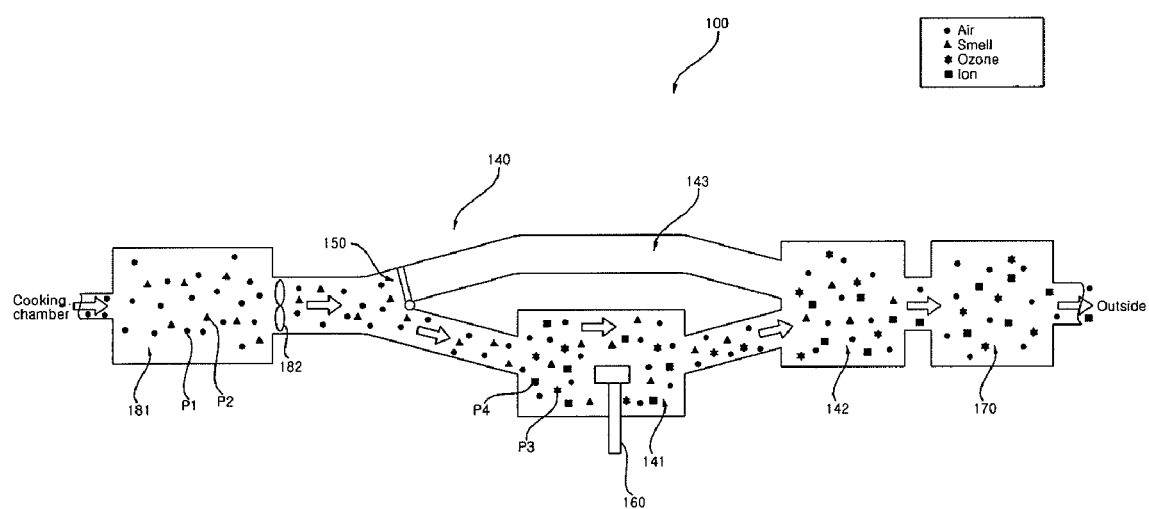
FIG. 7 is a schematic view illustrating the flow of air, odor-producing materials, ozone, and ions in a condition in which the inflow port of the bypass region is closed within the odor removal device of FIG. 2.

FIG. 7 schematically illustrates the flow state of the air P1, the odor-producing materials P2, the ozone P3, and the ions P4 with the inflow port 143a of the bypass region being closed. Referring to FIG. 7, in the cooking mode of the "strong" group, the controller 110 controls the flow control valve 150 to close the inflow port 143a of the bypass region. The odor-producing materials P2 generated from the cooking chamber 181 are in this way introduced to the first deodorization region 141. In the first deodorization region 141, the ozone P3 and the ions P4 are generated by a plasma discharge and function to remove the odor-producing materials P2. In the second deodorization region 142, the remaining odor-producing materials P2 are removed, and in the ozone removal unit 170, the remaining ozone P3 is removed. In the operating condition of the odor and odor-producing materials removal device 190 shown in FIG. 7, the odor-producing materials P2 are not introduced to the bypass region 143, so that a large amount of odor-producing materials P2 can be effectively removed.

Figure 8:
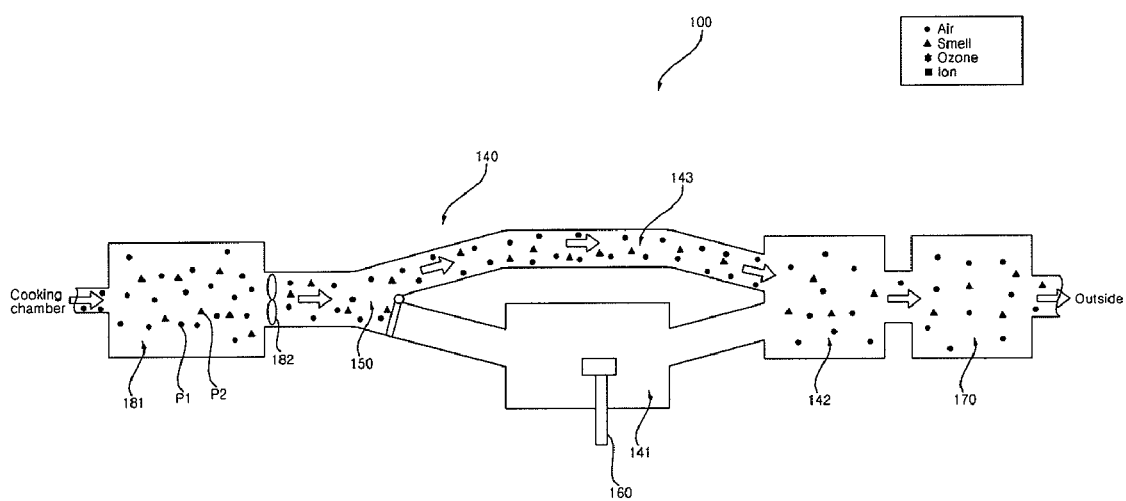
FIG. 8 is a schematic view illustrating the flow of air, odor and odor-producing materials, ozone, and ions in a condition in which the inflow port of the first deodorization region is closed within the odor removal device of FIG. 2.

FIG. 8 schematically illustrates the flow of the air P1 and the odor-producing materials P2 with the inflow port 141a of the first deodorization region being closed. Referring to FIG. 8, in the cooking mode of the "weak" group, the controller 110 controls the flow control valve to close the inflow port 141a of the first deodorization region. Accordingly, any odor-producing materials P2 generated from the cooking chamber 181 is introduced to the bypass region 143. Since the odor-producing materials P2 are not introduced to the first deodorization region 141, the plasma generator 160 does not operate. The odor-producing materials P2 are discharged to the outside through the second deodorization region 142 and the ozone removal unit 170. Since the plasma generator 160 does not operate, an ozone removal reaction does not occur in the ozone removal unit 170. At this time, the gas may not be introduced to the ozone removal unit 170, but may bypass the ozone removal unit 170 and be directly discharged to the outside. In the operating condition of the odor and odor-producing materials removal device 190 as shown in FIG. 8, the odor-producing materials P2 are not introduced to the first deodorization region 141. Consequently, exhaust can be smooth and the amount of power necessary for the cooling fan 182 can be decreased.

In accordance with the present invention, odor and odor-producing materials generated from a cooking chamber can be removed in a first deodorization region by a plasma discharge. Further, since an exhaust gas of the cooking chamber can bypass the first deodorization region and be discharged to the outside, exhaust can be smooth and consumption power can be decreased.

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

Although the invention has been described with reference to several exemplary embodiments, it is understood that the words that have been used are words of description and illustration, rather than words of limitation. As the present invention may be embodied in several forms without departing from the spirit or essential characteristics thereof, it should also be understood that the above-described embodiments are not limited by any of the details of the foregoing description, unless otherwise specified. Rather, the above-described embodiments should be construed broadly within the spirit and scope of the present invention as defined in the appended claims. Therefore, changes may be made within the metes and bounds of the appended claims, as presently stated and as amended, without departing from the scope and spirit of the invention in its aspects.

What is claimed is:

1. A cooking device, comprising:
   a cooking chamber;
   a first deodorization region along which air from the cooking chamber flows and in which a plasma discharge is generated for removing odor-producing materials generated in the cooking chamber from the air;
   a bypass region along which air from the cooking chamber flows to bypass the first deodorization region; and
   at least one flow control valve configured to adjust a first inflow amount of air from the cooking chamber into the first deodorization region and a second inflow amount of air from the cooking chamber into the bypass region.

2. The cooking device of claim 1, wherein the cooking device is a microwave oven.

3. The cooking device of claim 1, wherein the plasma discharge generates ozone and/or ions, and the ozone and/or ions remove the odor-producing materials from the air.

4. The cooking device of claim 3, further comprising:
   an ozone removal unit that removes the remaining ozone from the air downstream from the first deodorization region.

5. The cooking device of claim 1, further comprising a controller that controls the at least one the flow control valve to adjust the first inflow amount of air and the second inflow amount of air.

6. The cooking device of claim 5, wherein the controller controls the first at least one flow control valve based on operating information of the cooking device.

7. The cooking device of claim 6, wherein:
   the operating information includes a plurality of cooking modes of the cooking device, and
   the controller controls the at least one flow control valve based on the plurality of cooking modes.

8. The cooking device of claim 7, wherein:
   the plurality of cooking modes are classified into a plurality of groups based on a predicted discharge amount of odor-producing materials, and
   the controller controls the at least one flow control valve so that a ratio of the first inflow amount with respect to the second inflow amount increases for groups having larger predicted discharge amounts of odor-producing materials.

9. The cooking device of claim 5, further comprising:
   an input unit configured to receive instructions input by a user,
   wherein the controller controls the at least one flow control valve according to the instructions input by the user.

10. The cooking device of claim 1, further comprising a second deodorization region in which air from the first deodorization region which includes residual odor-producing materials is mixed with air from the bypass region which includes odor-producing materials, for removing the remaining odor-producing materials.

11. The cooking device of claim 10, wherein:
    the plasma discharge generated in the first deodorization region generates ozone and/or ions to remove odor-producing materials from the air, and
    the remaining ozone and/or the remaining ions from the first deodorization region remove the remaining odor-producing materials in the second deodorization region.

12. The cooking device of claim 11, further comprising an ozone removal unit that removes the remaining ozone in the air from the second deodorization region.

13. The cooking device of claim 1, wherein a flow rate of air in the first deodorization region is less than a flow rate of air in the bypass region.

14. The cooking device of claim 1, further comprising an outer casing, wherein the first deodorization region and the bypass region are located outside of the cooking chamber and inside of the outer casing.

15. The cooking device of claim 1, further comprising a plasma generator located in the first deodorization region, the plasma generator including first and second discharge electrodes separated by a dielectric material located there between.

16. A cooking device, comprising:
    a cooking chamber;
    a first deodorization region along which air from the cooking chamber flows to remove odor-producing materials generated in the cooking chamber from the air;
    a bypass region along which air from the cooking chamber flows to bypass the first deodorization region; and
    a flow control valve configured to adjust a first inflow amount of air from the cooking chamber into the first deodorization region and a second inflow amount of air from the cooking chamber into the bypass region.

17. A method for deodorizing air in a cooking device, comprising:
    exhausting air containing odor-producing materials from a cooking chamber of the cooking device;
    selectively directing the air from the cooking chamber to either a deodorization flow path or to a bypass flow path, or to both the deodorization flow path and the bypass flow path; and
    deodorizing air directed along the deodorization flow path by removing the odor-producing materials.

18. The method of claim 17, wherein the deodorizing includes generating plasma discharge to produce ozone and/or ions for removing the odor-producing materials from the air.

19. The method of claim 18, further comprising removing ozone remaining in the air downstream from the deodorization flow path.

20. The method of claim 17, wherein the selectively directing the air includes automatically directing the air based on a cooking mode of the cooking device.

21. The method of claim 17, wherein the selectively directing the air includes directing the air based on a selection input by a user.

* * * * *